US008236044B2

(12) United States Patent
Robaina (10) Patent No.: US 8,236,044 B2
(45) Date of Patent: Aug. 7, 2012

(54) STENT DESIGN WITH VARIABLE EXPANSION COLUMNS ALONG CIRCUMFERENCE (75) Inventor: Samuel Robaina, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1116 days.

(21) Appl. No.: 11/749,855

(22) Filed: May 17, 2007

(65) Prior Publication Data
US 2008/0004690 A1    Jan. 3, 2008

Related U.S. Application Data (60) Provisional application No. 60/818,012, filed on Jun. 30, 2006.

(51) Int. Cl.
A61F 2/06 (2006.01)
(52) U.S. Cl. ........................................ 623/1.15
(58) Field of Classification Search .............. 623/1.15, 623/1.16, 1.17, 1.18, 1.2, 23.7
See application file for complete search history.

(56) References Cited

U.S. PATENT DOCUMENTS

| 5,269,802 | A | * | 12/1993 | Garber | 623/1.15 |
| 6,264,685 | B1 | | 7/2001 | Ahari | |
| 6,706,062 | B2 | | 3/2004 | Vardi et al. | 623/1.15 |
| 6,776,793 | B2 | | 8/2004 | Brown et al. | 623/1.15 |
| 6,835,203 | B1 | | 12/2004 | Vardi et al. | 623/1.34 |
| 7,169,175 | B2 | * | 1/2007 | Cottone et al. | 623/1.22 |
| 7,204,848 | B1 | * | 4/2007 | Brown et al. | 623/1.15 |
| 7,341,598 | B2 | * | 3/2008 | Davidson et al. | 623/1.35 |
| 2004/0088044 | A1 | | 5/2004 | Brown et al. | 623/1.16 |
| 2004/0138737 | A1 | | 7/2004 | Davidson et al. | 623/1.35 |
| 2004/0176834 | A1 | | 9/2004 | Brown et al. | 623/1.15 |
| 2004/0181276 | A1 | | 9/2004 | Brown et al. | 623/1.16 |
| 2004/0230296 | A1 | | 11/2004 | Brown et al. | 623/1.16 |
| 2004/0267352 | A1 | | 12/2004 | Davidson et al. | 623/1.15 |
| 2005/0015139 | A1 | | 1/2005 | Brown et al. | 623/1.16 |
| 2006/0036315 | A1 | | 2/2006 | Yadin et al. | 623/1.35 |

FOREIGN PATENT DOCUMENTS

| EP | 1472990 A1 | 11/2004 |
| EP | 1 049 421 | 1/2005 |
| WO | 0067673 | 11/2000 |
| WO | 2007001519 A1 | 1/2007 |

OTHER PUBLICATIONS

U.S. Appl. No. 60/818,012, filed Jun. 30, 2006, Robaina.

* cited by examiner

Primary Examiner — Ryan Severson
Assistant Examiner — Jonathan W Miles
(74) Attorney, Agent, or Firm — Vidas, Arrett and Steinkraus (57) ABSTRACT A stent comprises at least one curve deployment section. The at least one curve deployment section comprises at least one expansion ring having a circumferential length, a longitudinal length and comprising a first circumferential section and a second circumferential section. The first circumferential section comprises an expansion column and the second circumferential section comprises at least two expansion columns longitudinally offset from one another. The expansion column of the first circumferential section is engaged to the at least two expansion columns of the second circumferential section.

20 Claims, 9 Drawing Sheets

STENT DESIGN WITH VARIABLE EXPANSION COLUMNS ALONG CIRCUMFERENCE

CROSS-REFERENCE TO RELATED APPLICATIONS

This Application claims priority from U.S. Application No. 60/818,012, filed on Jun. 30, 2006, the entire contents of which is hereby incorporated by reference.

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent has at least one curve deployment section. The curve deployment section has at least one expansion ring. The expansion ring has a circumferential length, a longitudinal length and at least two circumferential sections. Each circumferential section has a circumferential length so that the cumulative length equals the overall circumferential length of the expansion ring. The first circumferential section has one expansion column and the second circumferential section has at least two expansion columns.

In one embodiment, the at least two expansion columns of the second circumferential section are in phase with one another. In one embodiment, the at least two expansion columns of the second circumferential section are out of phase with one another.

In one embodiment, the longitudinal length of the expansion column of the first circumferential section is greater than the longitudinal lengths of the at least two expansion columns of the second circumferential section. In one embodiment, the longitudinal length of the expansion column of the first circumferential section is substantially the same as the longitudinal lengths of the at least two expansion columns of the second circumferential section.

In one embodiment, the curve deployment section has at least two expansion rings which are engaged to one another by connector struts.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment, a stent has at least one curve deployment section 10. A curve deployment section 10 is composed of at least one expansion ring 20 which is a radially expandable cylindrical element that extends about the circumference of the stent and has at least two circumferential sections 22. Each circumferential section 22 has at least one expansion column 24, with adjacent circumferential sections 22 within an expansion ring 20 have different a number of expansion columns 24. Thus, an expansion ring 20 has a variable number of expansion columns 24 about the circumference of the stent.

Figure 1:
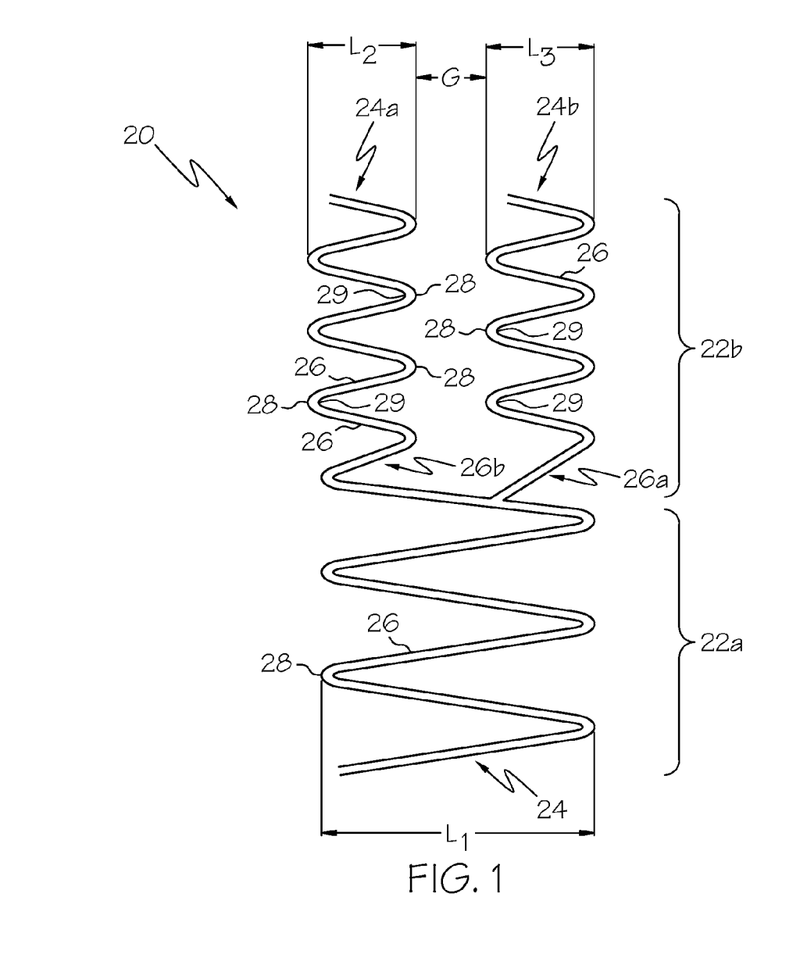
FIG. 1 is a flat view of a portion an embodiment of an expansion ring.

The expansion ring 20 can have a variety of configurations. FIG. 1 shows a portion of one embodiment of an expansion ring 20. The expansion ring 20 extends circumferentially about the stent and forms a part of the tubular body of the stent. Thus, the expansion ring 20 has a circumferential length and a longitudinal width. In this embodiment, the expansion ring 20 has a first circumferential section 22a and a second circumferential section 22b. In at least one embodiment, the expansion ring 20 has at least two circumferential sections 22. It is within the scope of the invention for the expansion ring 20 to have two, three, four, five, six, seven, eight or more circumferential sections 22.

Figure 6:
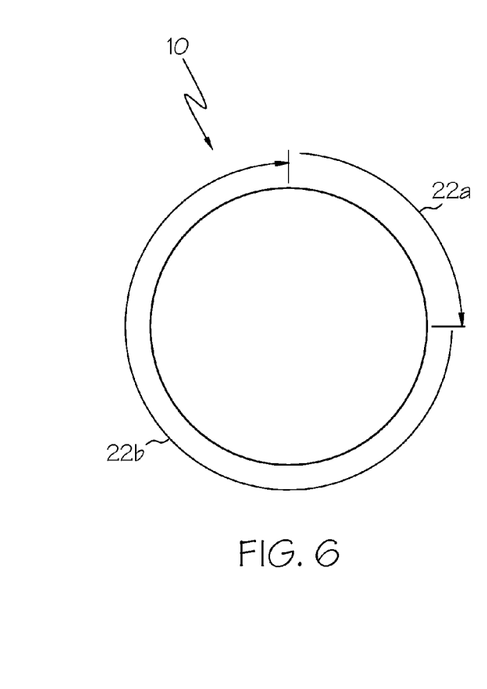
FIG. 6 is an end view of an embodiment of an expansion ring showing the circumferential positions of the two circumferential sections.

Each circumferential section 22 has a longitudinal length equal to the longitudinal length of the expansion ring 20. In addition, each circumferential section 22 has a circumferential length. Thus, the circumferential length of the expansion ring 20 is equal to the sum of the circumferential lengths of each circumferential section 22 of the expansion ring 20. Each circumferential section 22 also has a position about the circumference of the tubular body of the stent, a circumferential position. FIG. 6 is an end view of an expansion ring 20. If this view of the substantially circular tubular body is correlated to a clock, the circumferential position of the first circumferential section 22a would be from 12 to 3 while the circumferential position of the second circumferential section 22b would be from 3 to 12. Obviously, these positions are relative as the circumferential positions of the circumferential sections 22 depend on where 12 is determined to be located on the substantially circular tubular body. In addition, the circumferential positions depend upon the circumferential lengths of each circumferential section 22.

The first circumferential section 22a has one expansion column 24 while the second circumferential section 22b has two expansion columns 24a,b. The expansion column 24 of the first circumferential section 22a has a longitudinal length (L1) no greater than the longitudinal length of the expansion ring 20. FIG. 1 shows an expansion ring where the expansion column 24 of the first circumferential section 22a has a longitudinal length L1 substantially equal to the longitudinal length of the expansion ring 20. In essence, the longitudinal length of the expansion ring 20 is equal to the circumferential section 22 of the expansion ring 20 with the greatest longitudinal length.

Similarly, the longitudinal lengths (L2,L3) of the expansion columns 24a,b of the second circumferential section 22b and the longitudinal gaps (G) between the expansion columns 24a,b have a cumulative longitudinal length no greater than the longitudinal length of the expansion ring 20. The longitudinal gap (G) is the longitudinal length or distance between the distal end of the first expansion column 24a and the proximal end of the second expansion column 24b, as illustrated in FIG. 1. Also, the expansion columns 24a,b of the second circumferential section 22b have a longitudinal length (L2, L3) less than the longitudinal length of the expansion column 24 of the first circumferential section 22a.

Also note in FIG. 1, that strut 26a, which engages the second expansion column 24b of the second circumferential section 22b to the first circumferential section 22a, is longer than strut 26b which engages the first expansion column 24a of the second circumferential section 22b to the first circumferential section 22a. Note that strut 26b is substantially the same length as the other expansion column struts 26. This difference in strut length 26a, 26b enables the expansion columns 24a,b of the second circumferential section 22b to be in phase with one another.

When expansion columns 24 are in phase, the expansion column peaks 28 correlate with one another so that the expansion column peaks 28 are in the same direction, thereby forming a synchronized pattern. Thus for example, all the expansion column peaks 28 at a particular circumferential location extend in one direction, e.g. distally, and all the expansion column peaks 28 at the adjacent circumferential location extend in a different location, e.g. proximally.

Figure 7:
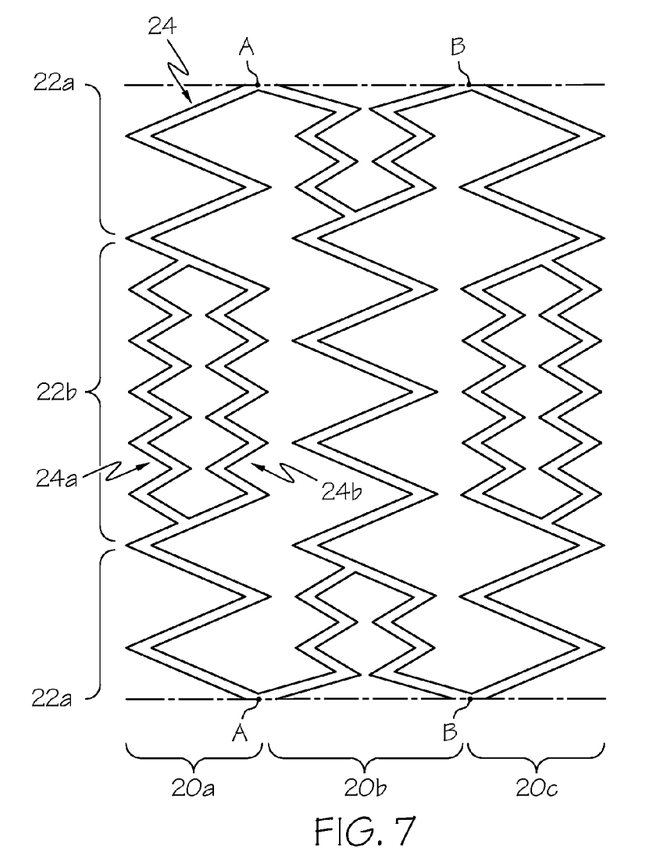
FIG. 7 is flat view of an embodiment of a curve deployment section without connectors so that the three expansion rings are connected only at points A and B.

It is also within the scope of the invention for the expansion columns to be out of phase with one another, as illustrated in FIG. 7. Therefore, expansion column peaks 28 at the same circumferential position are 180 degrees out of phase with one another. Thus, the expansion column peaks 28 of one expansion columns 24a extends one direction, e.g. distally, while the expansion column peaks 28 of the adjacent expansion column 24b extends in the opposite direction, e.g. proximally.

Figure 2:
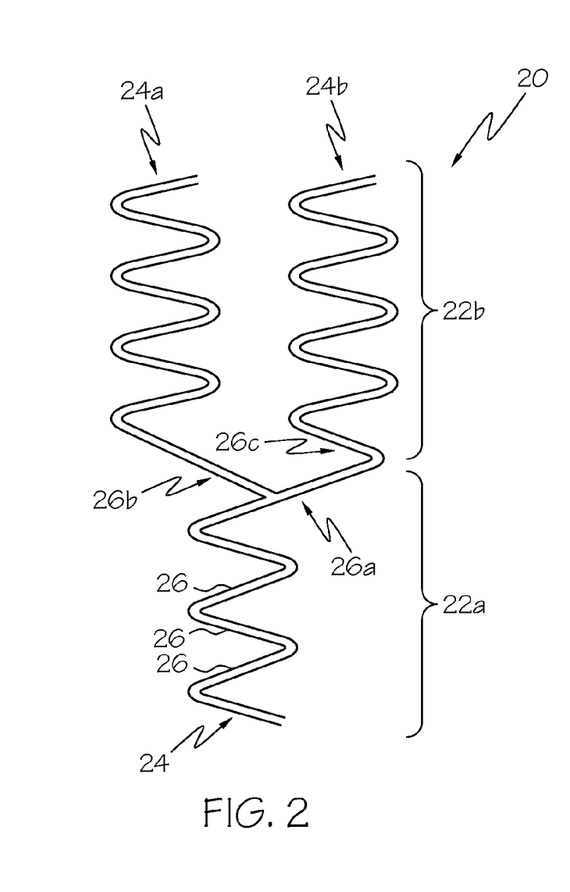
FIG. 2 is a flat view of a portion of an alternative embodiment of an expansion ring.

FIG. 2 shows an embodiment where the longitudinal lengths of the expansion columns 24 of the first circumferential section 22a and the second circumferential section 22b are each less than the longitudinal length of the expansion ring 20. In addition, the longitudinal length of the expansion column 24 of the first circumferential section 22a is substantially equal to the longitudinal lengths of the expansion columns 24a,b of the second circumferential section 22b. Strut 26a is longer than the other struts 26 of the expansion column 24 of the first circumferential section 22a. This allows the expansion column 24 of the first circumferential section 22a to have a smaller longitudinal length and yet still engage the expansion columns 24a,b of the second circumferential section 22b. Similar to FIG. 1, the struts 26b and 26c have different lengths which allow the two expansion columns 24a,b of the second circumferential section 22b to be in phase with one another.

Figure 3:
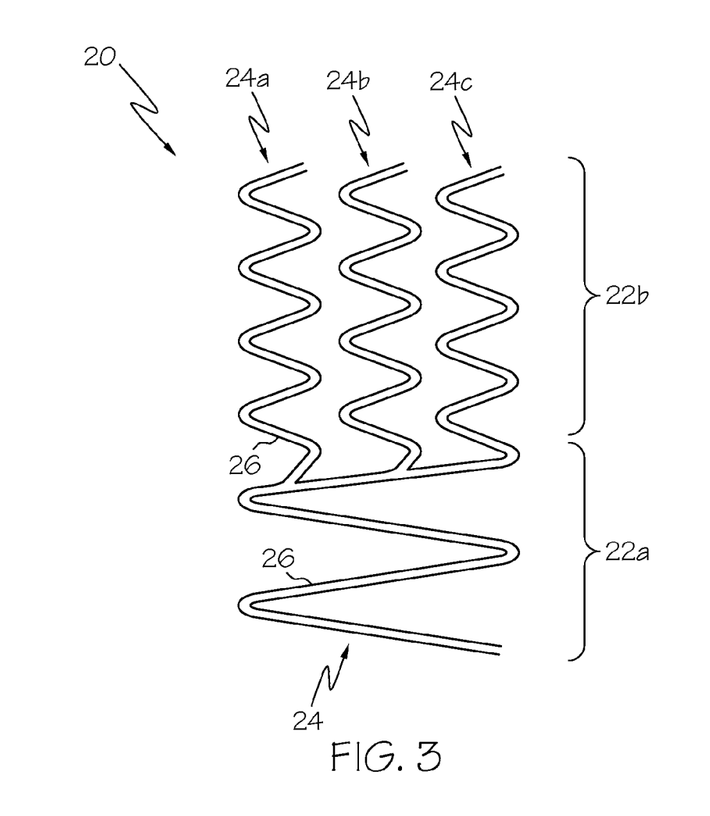
FIG. 3 is a flat view of a portion of an embodiment of an expansion ring with three expansion columns in the second circumferential section.
Figure 4:
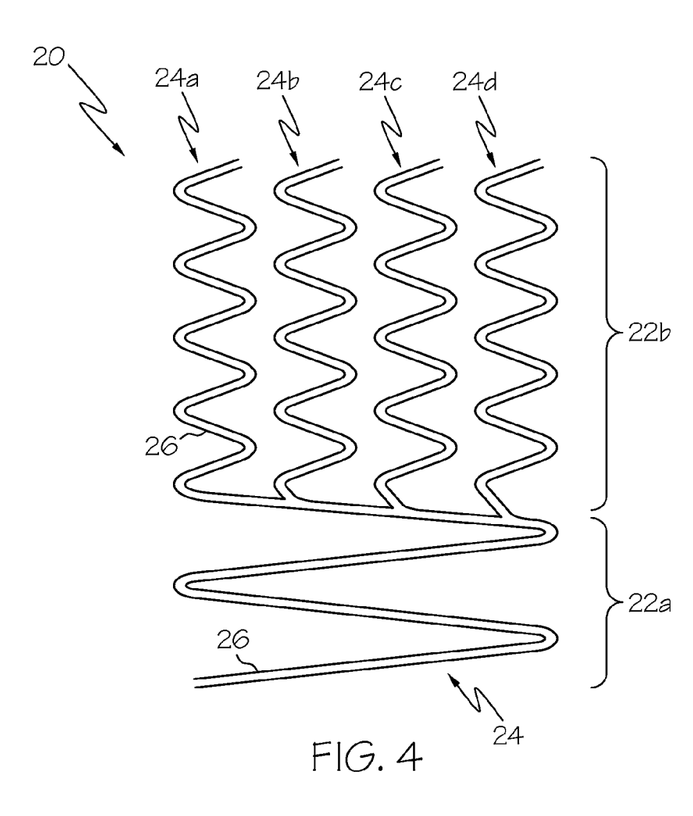
FIG. 4 is a flat view of a portion of an embodiment of an expansion ring with four expansion columns in the second circumferential section.

Although the second circumferential sections 22b of FIGS. 1 and 2 have two expansion columns 24a,b, it is within the scope of the invention for the second circumferential section 22b to have two, three, four, five, six, seven, eight, nine, ten or more expansion columns 24. FIG. 3 shows an embodiment where the second circumferential section 22b has three expansion columns 24a,b,c and FIG. 4 shows an embodiment where the second circumferential section 22b has four expansion columns 24a,b,c,d.

Each expansion column 24 is comprised of struts 26 and peaks 28/valleys 29. The pattern formed by the struts and peaks 28/valleys 29 in FIG. 1 is a serpentine pattern but any pattern can be formed by the struts and peaks 28/valleys 29. For example, the expansion column 24 of FIG. 7 has a zig-zag pattern. Each strut 26 has a longitudinal length and the longitudinal length of the expansion column 24 depends on the length of the struts 26 forming the expansion column 24. In order for the expansion columns to expand evenly, the strut dimensions or aspect ratio need to be optimized. Thus, expansion columns with a longer circumferential length have different strut dimensions, i.e. strut width and/or strut thickness, than expansion columns with a shorter circumferential length. If the diameter of the strut is substantially constant, for example with struts that are round, then the strut diameter needs to be optimized. In addition, the strut peaks, including the peak radius need to be optimized.

Figure 5:
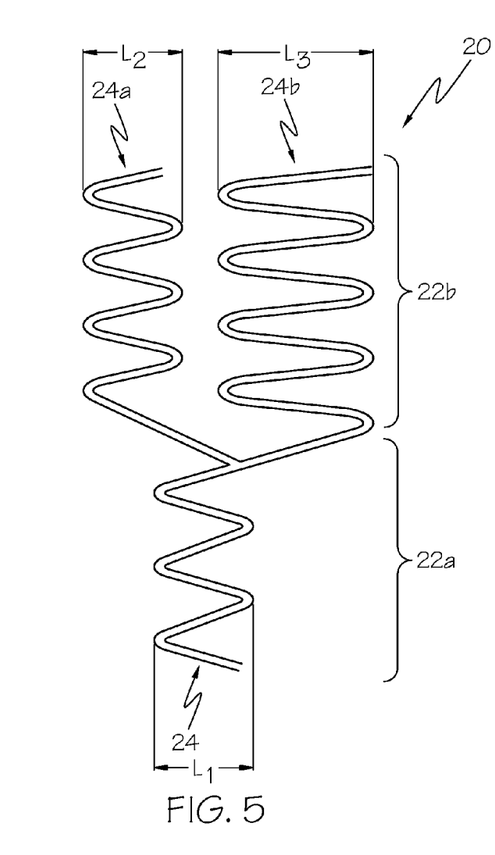
FIG. 5 is a flat view of a portion of an embodiment of an expansion ring where the expansion columns in the second circumferential section have different longitudinal lengths.

In at least one embodiment, the expansion columns 24 of the second circumferential section 22b have at least two longitudinal lengths L2,L3, as shown in FIG. 5. The first expansion column 24a has a longitudinal length L2 and the second expansion column 24b has a longitudinal length L3. The expansion column 24 of the first circumferential section 22a has a longitudinal length of L1.

There can be many relationships between the longitudinal lengths, L1, L2 and L3 of the expansion columns 24. In one embodiment, the longitudinal lengths, L1, L2 and L3 of the expansion columns 24 are different from one another. In at least one embodiment, the longitudinal lengths L1, L2 and L3 of the expansion columns 24 are substantially the same, as shown in FIG. 2. In at least one embodiment, the longitudinal lengths L1 and L2 of the expansion columns 24 are substantially the same but less than the longitudinal length L3, as shown in FIG. 5. In at least one embodiment, the longitudinal lengths L2 and L3 of the expansion columns 24 of the second circumferential section 22b are substantially the same but less than longitudinal length L1, as shown in FIG. 1. Obviously, the combinations are numerous when the second circumferential section 22b has more than two expansion columns 24.

In addition, the whether the stent is in an unexpanded or an expanded state can also affect the relationship between the longitudinal lengths of the first and second circumferential sections. In at least one embodiment, the ratio of the longitudinal lengths between the first circumferential section 22a and the second circumferential section 22b changes when the stent goes from the as cut state/unexpanded state, to the deployed/expanded state. Thus, in one embodiment, the longitudinal length of the first circumferential section 22a is different (either greater or smaller) than the circumferential length of the second circumferential section 22b in the unexpanded state, but in the expanded state, the longitudinal length of the first circumferential section 22a is equal to the longitudinal length of the second circumferential section 22b. In one embodiment, in the expanded state, the longitudinal length of the first circumferential section 22a is different than the longitudinal length of the second circumferential section 22b but the difference between the two has changed (either a greater difference or a smaller difference).

FIG. 7 is a flat view of an embodiment of a curve deployment section 10 of a stent. In at least one embodiment, the stent consists only of a curve deployment section 10. It is within the scope of the invention for a stent to have one, two, three, four, five, six or more curve deployment sections 10. The curve deployment section(s) 10 can be positioned anywhere along the longitudinal length of the stent. The curve deployment section 10 is engaged to the other section(s) of the stent by connectors 30 to form the complete stent.

The curve deployment section 10 can have any number of expansion rings 20. Thus, it is within the scope of the invention for the curve deployment section 10 to have one, two, three, four, five, six, seven, eight, nine, ten or more expansion rings 20. In the embodiment shown in FIG. 7, the curve deployment section 10 has three expansion rings 20. In one embodiment, the curve deployment section 10 has at least one expansion ring 20.

In this embodiment, the three expansion rings 20a,b,c are connected to one another at A and B to form a tubular structure. Connections A and B are the only means by which the expansion rings 20a,b,c of the curve deployment section 10 are engaged to one another because there are no connector struts 30. Except for the zig-zag pattern and lack of connector struts 30, this curve deployment section 10 has the same attributes as the curve deployment section 10 of FIG. 10, which is discussed in detail below.

Figure 8:
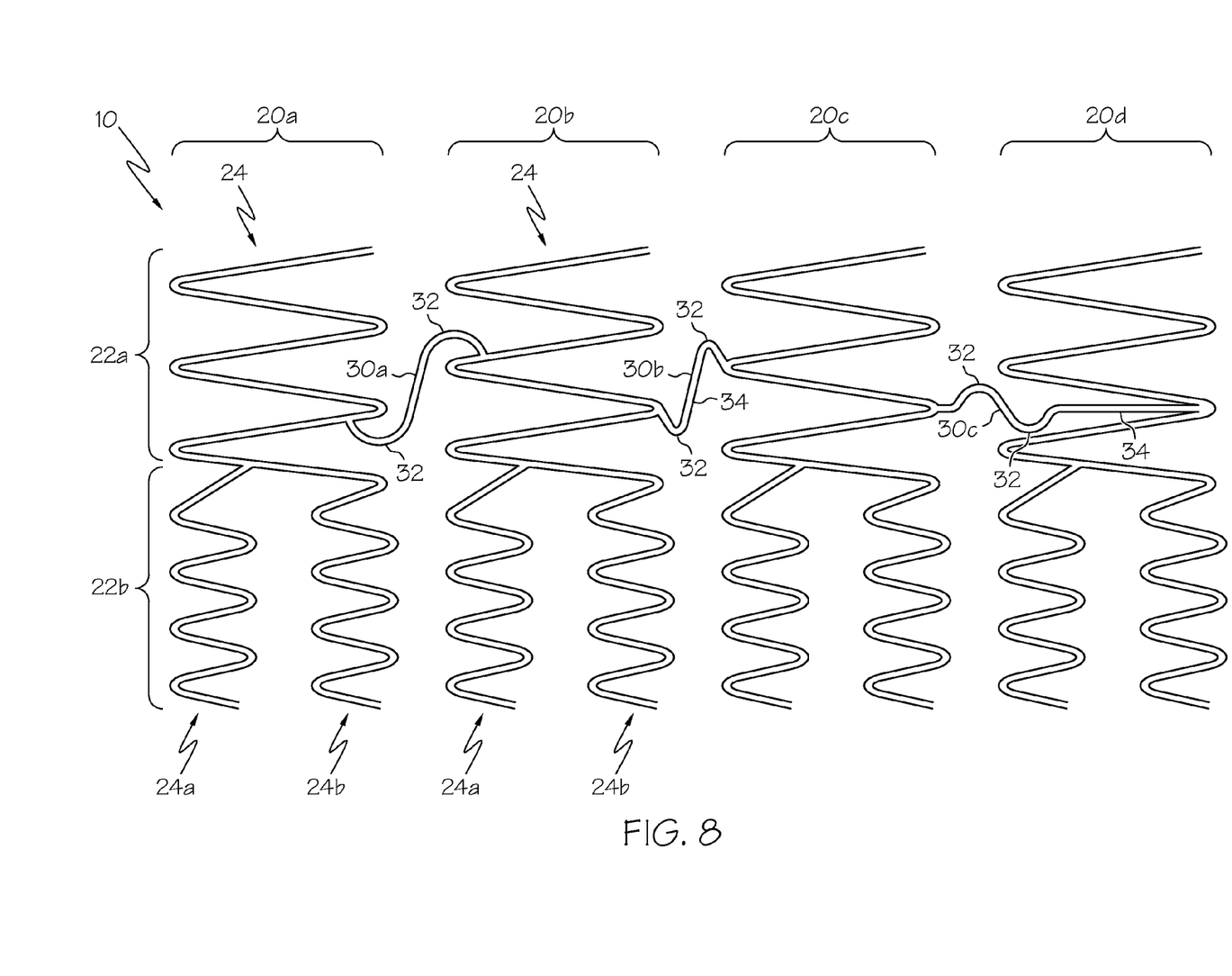
FIG. 8 is a flat view of an embodiment of a curve deployment section with connectors.

FIG. 8 is an embodiment of a curve deployment section 10 with four expansion rings 20 with connectors 30 that engage adjacent expansion rings 20. Each of the four expansion rings 20 has a first circumferential section 22a and a second circumferential section 22b. The first circumferential sections 22a and the second circumferential section 22b of each expansion ring 20 have the same circumferential position. The expansion columns 24 of the first circumferential sections 22a of each expansion ring 20 are in phase with one another. The second circumferential sections 22b of each expansion ring 20 have two expansion columns 24a,b which are in phase with one another. In addition, the expansion columns 24a,b of adjacent expansion rings 20 are in phase with one another. In this embodiment, the similar alignment of the expansion columns 24 maximizes flexibility and conformability in a single bending moment because the configurations of the four expansion rings 20 are identical.

Figure 9:
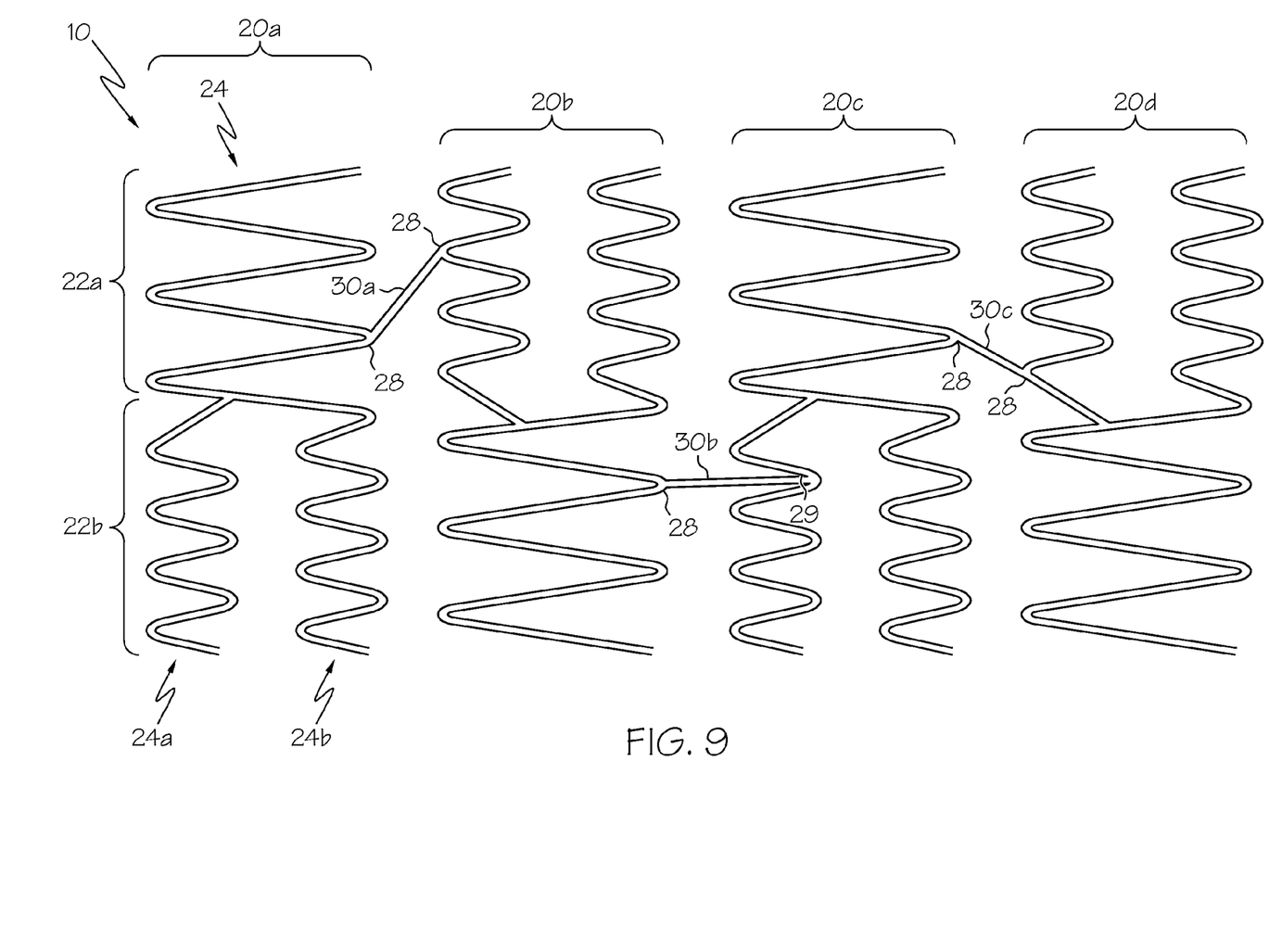
FIG. 9 is a flat view of an alternative embodiment of a curve deployment section with connectors.

A second embodiment of the curve deployment section 10 is shown in FIG. 9. In this embodiment, the four expansion rings 20 of a curve deployment section 10 have alternating configurations, i.e. the first and third expansion ring 20a,c have the same configuration while the second and fourth expansion ring 20b,d have a configuration that is opposite of the first and third expansion ring 20a,c configuration. Thus, where one expansion ring 20a has a first circumferential section 22a at a particular circumferential position, the adjacent expansion ring 20c has a second circumferential section 22b at the same circumferential position. This embodiment provides more conformability in several bending moments due to the alternating configurations of the expansion rings 20. The conformability in a bending moment is provided by the circumferential sections(s) 22 of the expansion ring 20 that have at least two expansion columns 24.

The configuration of the curve deployment section 10 shown in FIG. 9 can be achieved in several ways. In at least one embodiment, the first circumferential sections 22a and the second circumferential sections 22b of the expansion rings 20 have the same circumferential length. In at least one embodiment, the expansion rings 20 have at least two circumferential sections 22, a first circumferential section 22*a* and a second circumferential section 22*b* with the substantially the same circumferential length and the first and second circumferential sections 22*a,b* alternate about the circumference. In at least one embodiment, the first circumferential section 22*a* has a smaller circumferential length than the second circumferential section 22*b*.

Figure 10:
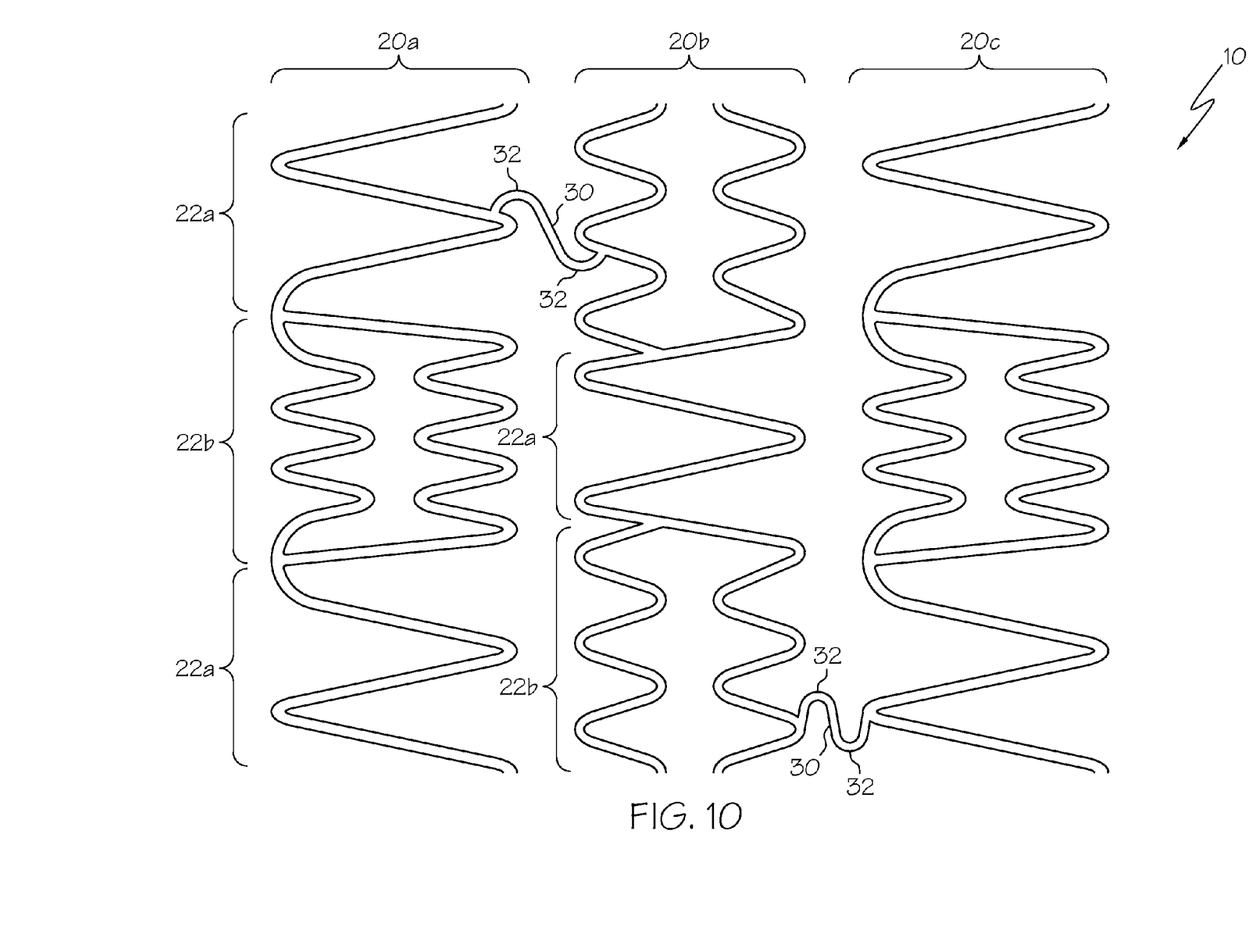
FIG. 10 is a flat view of an alternative embodiment of a curve deployment section with connectors.
Figure 11:
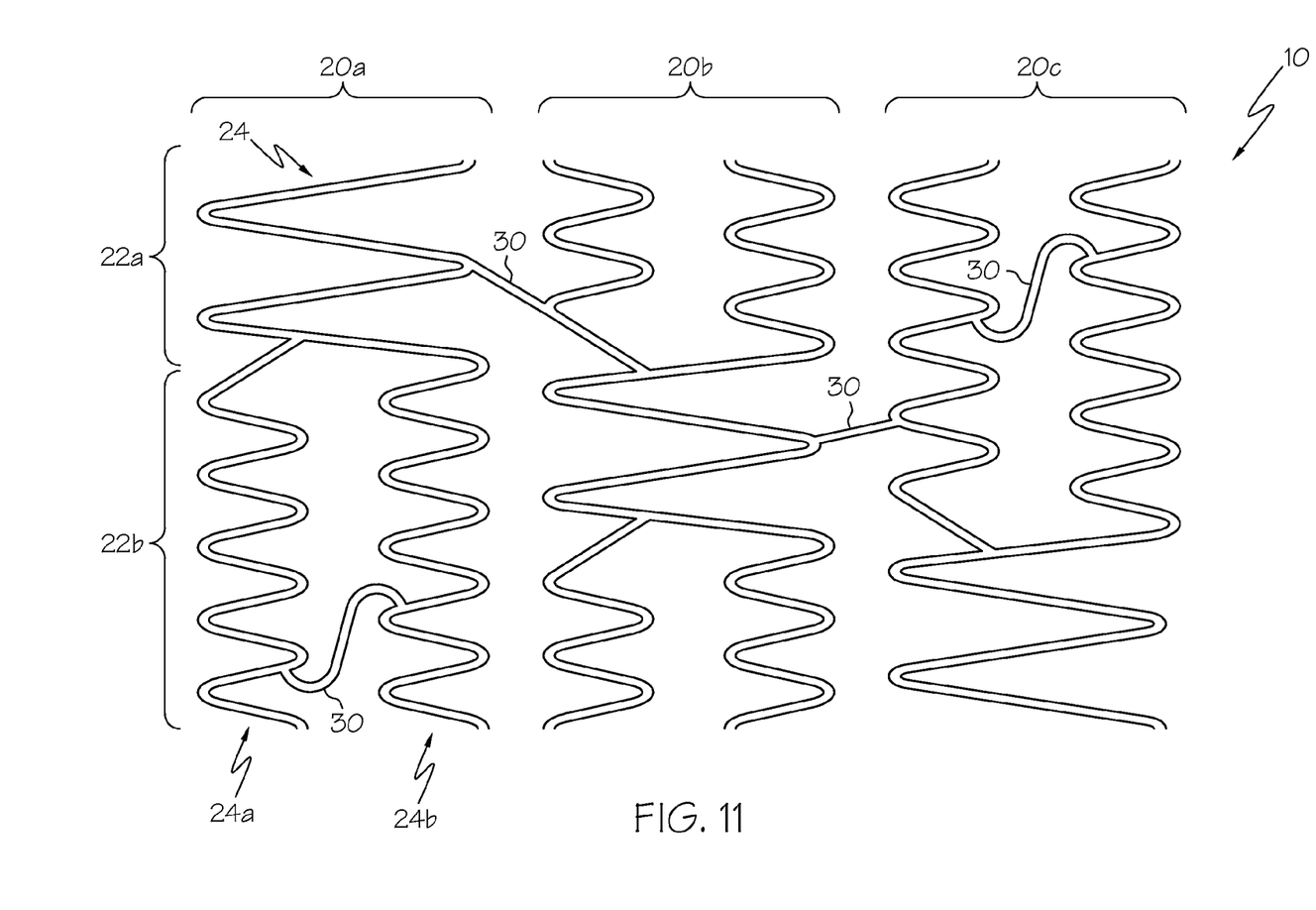
FIG. 11 is a flat view of an alternative embodiment of a curve deployment section with connectors.

The order and design of the expansion columns 24 can be varied to optimize scaffolding depending upon the anatomical application or extent of disease as is shown in FIGS. 10 and 11. In FIG. 10, the expansion rings 20 have alternating configurations so that the first and third expansion ring 20*a,c* have the same configuration while the second expansion ring 20*b* has a different configuration. Thus, the first expansion ring 20*a* has a first circumferential section 22*a* at a particular circumferential position while the second expansion ring 20*b* has a second circumferential section 22*b* at that same circumferential position. Alternating the configurations of the expansion rings 20 can be continued for all the expansion rings 20 of a curve deployment section 10 or for as many of the expansion rings 20 of a curve deployment section 10 as desired.

The configuration of the curve deployment section 10 shown in FIG. 10 can be achieved in several ways. In at least one embodiment, the expansion rings 20 of the curve deployment section 10 have only two circumferential sections 22 where the first circumferential section 22*a* of the first and third expansion rings 20*a,c* has a substantially larger circumferential length than the second circumferential section while the first circumferential section 22*a* of the second expansion ring 20*b* has a substantially smaller circumferential length than the second circumferential section 22*b*.

In at least one embodiment, the expansion rings 20 of the curve deployment section 10 have at least two circumferential sections 22, a first circumferential section 22*a* and a second circumferential section 22*b* where the lengths of the first and second circumferential sections 22*a,b* are substantially the same and the first and second circumferential sections 22*a,b* alternate about the circumference of the stent.

An alternative embodiment of a curve deployment section 10 is shown in FIG. 11. In this embodiment, the expansion ring 20 has only two circumferential sections 22, the first circumferential section 22*a* and the second circumferential section 22*b*. The first circumferential section 22*a* has one expansion column 24 and the second circumferential section 22*b* has two expansion columns 24*a,b*. The first circumferential section 22*a* has a shorter circumferential length than the second circumferential section 22*b*. In addition, the position of the first circumferential section 22*a* varies in the three expansion rings 20*a,b,c* so that the first circumferential sections 22*a* of the expansion rings 20*a,b,c* have a consecutive circumferential position in relation to the first circumferential section 22*a* of the adjacent expansion ring 20*a,b,c*. Thus, if the circumferential positions of the first circumferential sections 22*a* of the three adjacent expansion rings 20*a,b,c* were described in relation to a clock, as shown in FIG. 6, the circumferential positions could span from 12 to 1, from 1 to 2, and from 2 to 3 for the first, second and third expansion rings 20*a,b,c* respectively.

In at least one embodiment, the first circumferential sections 22*a* of adjacent expansion rings 20 circumferentially offset from one another by a pre-determined circumferential distance. In this embodiment, if the circumferential positions of the first circumferential sections 22*a* of the three adjacent expansion rings 20 were described in relation to a clock, the circumferential positions could span from 12 to 1, from 12:30 to 1:30 and from 1 to 2, respectively. Alternatively the positions could span from 12 to 1, from 2 to 3 and from 4 to 5, respectively.

In at least one embodiment, adjacent expansion rings 20 are connected by at least one connector strut 30. In some embodiments, the at least one connector strut 30 is arranged so that flexibility of the curve deployment section 10 is minimized. A large number of connector struts 30 can minimize the flexibility of the curve deployment section 10. In at least one embodiment, adjacent first circumferential sections 22*a* are engaged to one another by connectors 30, as illustrated in FIG. 8. In at least one embodiment, connectors 30 engage adjacent circumferential sections 22*a,b* which are different from one another, as illustrated for example in FIG. 9. In at least one embodiment, the curve deployment section 10 has connectors 30 between adjacent expansion rings 20 and between adjacent expansions columns 24 within a circumferential section 22 that has at least two expansion columns 24, as illustrated in FIG. 11. In at least one embodiment, a curve deployment section 10 is engaged to another section of the stent by at least one connector 30.

The connectors 30 can have any shape and can engage adjacent expansion rings 20 in any manner. It is within the scope of the invention for the connector strut 30 to have any configuration, including but not limited to, straight, curvilinear, and zig-zag. In FIG. 8, the connectors 30 have at least one curve 32. A curve may be sharp, as in a zig-zag, or more rounded, like the curves 32 in the first connector 30*a*. The first connector 30*a* extends from an expansion column strut 26 on one expansion ring 20*a* to an expansion column strut 26 on the adjacent expansion ring 20*b*. The second connector 30*b* extends from an expansion column peak 28 on one expansion ring 20*b* to an expansion column peak 28 on the adjacent expansion ring 20*c*, a peak to peak connector. The second connector 30*b* has two curves 32 and one straight segment 34. The third connector 30*c* extends from an expansion column peak 28 on one expansion ring 20*c* to an expansion column valley 29 on the adjacent expansion ring 20*d*, a peak to valley connector. The third connector 30*c* has two curves 32 and one straight segment 34. In FIG. 9, all the connectors 30 are straight and have no curves 32. Connectors 30*a* and 30*c* extend from an expansion column peak 28 on one expansion ring 20 to an expansion column peak 28 on the adjacent expansion ring 20. Connector 30*b* extends from an expansion column peak 28 on one expansion ring 20 to an expansion column valley 29 on the adjacent expansion ring 20. It is also within the scope of the invention for the connector to be a valley to valley connector.

Figure 12:
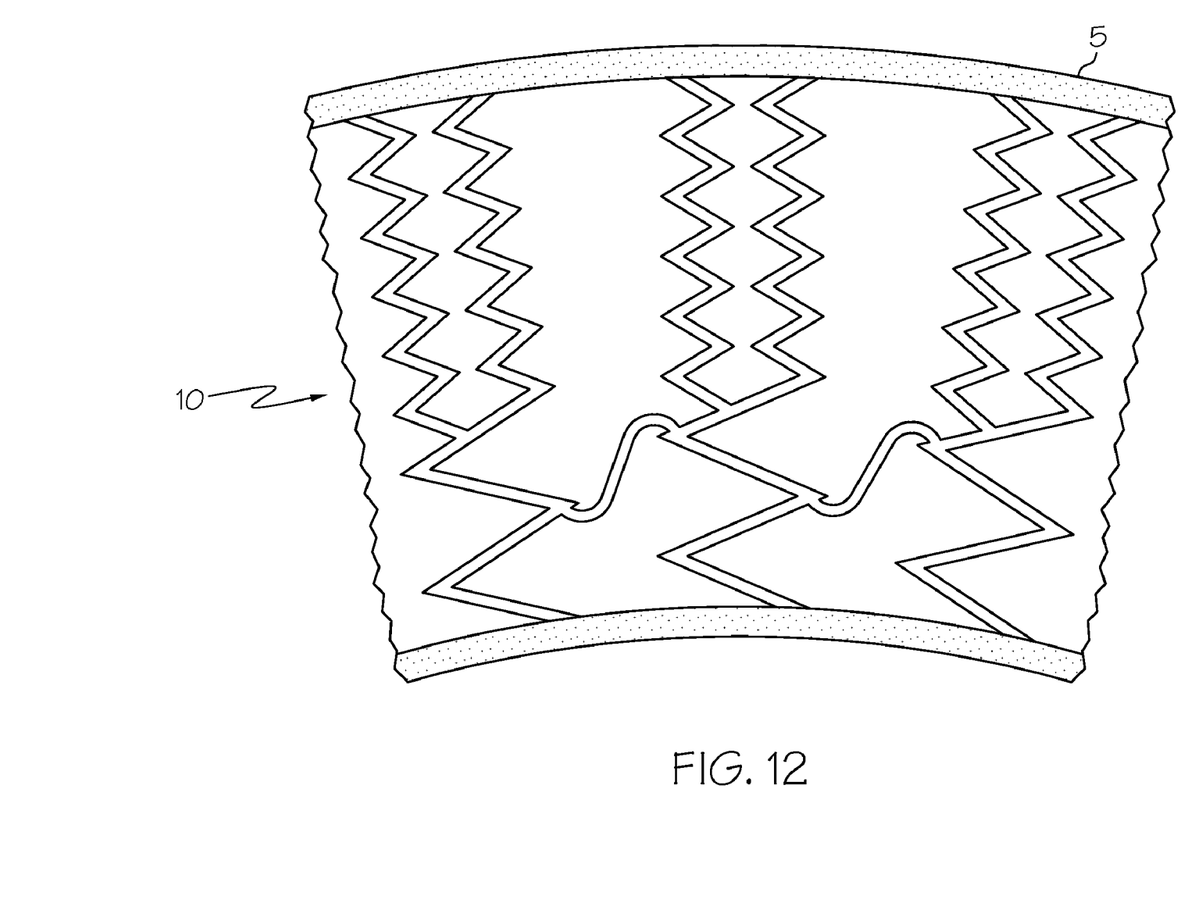
FIG. 12 is a view of an embodiment of a curve deployment section in an expanded state within a vessel curve.

An illustration of how a curve deployment section 10 would look in an expanded state within a curved vessel 5 is shown in FIG. 12. When the curve deployment section 10 is in an expanded state, the variable number of expansion columns 24 can provide the stent with several advantages. In some embodiments, a variable number of expansion columns 24, about the circumference of the stent, increases the uniformity of drug delivery in a curved portion of a blood vessel due to the decreased longitudinal separation of adjacent expansion columns 24. In some embodiments, a variable number of expansion columns 24, about the circumference of the stent, increases the amount of scaffolding in a curved portion of a blood vessel due to the decreased longitudinal separation of adjacent expansion columns 24. In some embodiments, the longitudinal flexibility of the stent is increased due to the increased number of expansion columns 24 per unit of longitudinal length of the stent.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS) polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising at least one curve deployment section, the at least one curve deployment section comprising a first expansion ring and a second expansion ring, each expansion ring having a circumferential length, a longitudinal length and comprising a first circumferential section and a second circumferential section, the first circumferential section comprising an expansion column, the second circumferential section comprising at least two expansion columns longitudinally offset from one another, the expansion column of the first circumferential section engaged to the at least two expansion columns of the second circumferential section.

2. The stent of claim 1, each expansion column having a longitudinal length, the longitudinal length of each of the at least two expansion columns of the second circumferential section less than the longitudinal length of the expansion ring.

3. The stent of claim 2, the longitudinal length of the expansion column of the first circumferential section substantially equal to the longitudinal length of the expansion ring.

4. The stent of claim 2, the longitudinal length of each expansion column being substantially the same.

5. The stent of claim 1, further comprising at least one connector strut.

6. The stent of claim 5, the at least one connector strut engaging adjacent expansion rings.

7. The stent of claim 5, the at least one connector strut engaging adjacent expansion columns of the second circumferential section.

8. The stent of claim 1, each of the circumferential sections having a circumferential position, the first circumferential sections of each expansion ring having the same circumferential position and the second circumferential sections of each expansion ring having the same circumferential position.

9. The stent of claim 8, the first circumferential sections being in phase and the second circumferential sections being in phase.

10. The stent of claim 1, the at least one curve deployment section further comprising a third expansion ring and a fourth expansion ring, each of the circumferential sections having a circumferential position, the first circumferential sections of the first and third expansion rings having the same circumferential position as the second circumferential sections of the second and fourth expansion rings, the second circumferential sections of the first and third expansion rings having the same circumferential position as the first circumferential sections of the second and fourth expansion rings.

11. The stent of claim 10, the first circumferential sections being in phase and the second circumferential sections being in phase.

12. The stent of claim 1, each expansion ring having a plurality of alternating first and second circumferential sections, each circumferential section having a circumferential position, the first circumferential sections of each expansion ring having the same circumferential positions.

13. The stent of claim 12, the first circumferential sections of adjacent expansion rings having a phase relationship that is the same and the second circumferential sections of adjacent expansion rings having a phase relationship that is the same.

14. The stent of claim 12, each second circumferential section having a plurality of expansion columns, the plurality of expansion columns being out of phase with each other.

15. The stent of claim 12, further comprising at least one connecting strut, the at least one connector strut engaging adjacent expansion rings.

16. The stent of claim 1, the first circumferential sections of the expansion rings having consecutive circumferential positions.

17. The stent of claim 16, the first circumferential sections being in phase and the second circumferential sections being in phase.

18. The stent of claim 1, the at least one curve deployment section further comprising a third expansion ring, the first, second and third expansion rings engaged at least two locations so that the expansion rings form a tubular structure.

19. The stent of claim 1 further comprising at least one radiopaque marker.

20. The stent of claim 1 further comprising a therapeutic agent, the therapeutic agent selected from at least one member of the group consisting of a non-genetic therapeutic agent, a genetic therapeutic agent, cellular material, a polymer agent, and any combination thereof.

* * * * *